United States Patent
Walker et al.

(10) Patent No.: US 7,122,532 B2
(45) Date of Patent: *Oct. 17, 2006

(54) REGULATION OF INTRACELLULAR GLUCOCORTICOID CONCENTRATIONS

(75) Inventors: Brian Robert Walker, Edinburgh (GB); Christopher Richard Watkin Edwards, London (GB); Jonathan Robert Seckl, Edinburgh (GB)

(73) Assignee: The University of Edinburgh, Edinburgh (GB)

( * ) Notice: Subject to any disclaimer, the term of this patent is extended or adjusted under 35 U.S.C. 154(b) by 209 days.

This patent is subject to a terminal disclaimer.

(21) Appl. No.: 10/080,876

(22) Filed: Feb. 22, 2002

(65) Prior Publication Data

US 2002/0128246 A1    Sep. 12, 2002

Related U.S. Application Data

(62) Division of application No. 09/029,535, filed as application No. PCT/GB96/02134 on Aug. 28, 1996, now Pat. No. 6,368,816.

(30) Foreign Application Priority Data

Aug. 29, 1995  (GB) .................................. 9517622.8

(51) Int. Cl.
    *A61K 31/56*    (2006.01)
(52) U.S. Cl. ...................... 514/169; 425/25; 514/548
(58) Field of Classification Search ................ 514/548, 514/177, 169; 425/25
    See application file for complete search history.

(56) References Cited

U.S. PATENT DOCUMENTS 5,128,150 A    7/1992    Shanbrom
6,368,816 B1 *  4/2002    Walker et al. ................. 435/25

FOREIGN PATENT DOCUMENTS

WO    97/07789    3/1997

OTHER PUBLICATIONS

Walker et al., Clinical Endocrinology 1993, pp. 221-227.*
Stewart et al., J. Steroid Biochem. Molec. Bio. vol. 40, No. 4-6, pp. 501-509, 1991.*
Goodman and Gilmans, The pharmacological Basis of Therapeutics 7 th Edition, pp. 1463-1473.*
ACTH; Adrenocortical Steroids: Inhibitors Of Biosynthesis, Chapter 63, p. 1463-1473.

International Classification Of Diseases—10 (1992); pp. 332-337. Endocrinology and Metabolism, Part Thirteen, Chapter 335, p. 1960-1965.
Anil K. Agarwalt, et al., Cloning And Expression Of Rat cDNA Endcoding Corticosteroid 11β-Dehydrogenase, Journal of Biological Chemistry (1989), vol. 364, No. 32, p. 18939-18943.
Olusola A. Ajilore, et al., In Vivo Characterization Of 11β-Hydroxysteroid Dehydrogenase In Rat Hippocampus Using Glucocorticoid Neuroendangerment As an Endpoint, Neuroendocrionology (1999): 69, p. 138-144.
Robert C. Andrews, et al., Effects Of the 11β-Hydroxysteroid Dehydrogenase Inhibitor Carbenoxolone On Insulin Sensitivity In Men With Type 2 Diabetes, Journal of Clinical Endocrinology & Metabolism (2003): 88, (1), p. 285-291.
J.A. Atiea, et al., Early Morning Hyperglycaemia "Dawn Phenomenon" In Non-Insulin Dependent Diabetes Mellitus (NIDDM): Effects Of Cortisol Suppression By Metyrapone, Diabetes Research (1990): 14, p. 181-185.
C.G. Beardwell, et al., Prolonged Remission In Florid Cushing's Syndrome Following Metyrapone Treatment, Clinical Endocrinology (1981): 14, p. 485-492.
Andrew S. Brem, et al. Bidirectional Activity Of 11β-Hydroxysteroid Dehydrogenase In Vascular Smooth Muscle Cells, Steroids (1995): 60, p. 406-410.
C. Calle, et al., Decreased Insulin Binding And Antilipolytic Response In Adipocytes From Patients With Cushing's Syndrome, Bioscience Reports (1987) vol. 7, No. 9, p. 713-718.
C. Calle, et al., Binding And Antilipolytic Action Of Insulin In Isolated Adipocytes From Cortisol-Treated Rats, Revista Espanola De Fisiologia (1988) vol. 44, No. 3, p. 309-314.
S. Diederich, et al., In The Search For Specific Inhibitors Of Human 11β-Hydroxysteroid-Dehydrogenases (11β-HSDs): Chenodeoxycholic Acid Selectively Inhibits 11β-HSD-I, European Journal Of Endocrinology (2000) vol. 142, p. 200-207.
J. Donckier, et al., Successful control Of Cushing's disease In the Elderly With Long Term Metyrapone, Postgraduate Medical Journal (1986) vol. 62, p. 727-730.
D. Englehardt, et al., Therapy Of Cushing's Syndrome With Steroid Biosynthesis Inhibitors, J. Steroid Biochem. Molec. Biol. (1994) vol. 49, No. 4-6, p. 261-267.

(Continued)

*Primary Examiner*—Sreeni Padmanabhan
*Assistant Examiner*—Shobha Kantamneni
(74) *Attorney, Agent, or Firm*—Frommer Lawrence & Haug LLP; Thomas J. Kowalski; Angela M. Collison

(57) ABSTRACT

This invention relates to the interconversion of inactive 11-keto steroids with their active 11B-hydroxy equivalents, to methods by which the conversion of the inactive to the active form may be controlled, and to useful therapeutic effects which may be obtained as a result of such control. More specifically, but not exclusively, the invention is concerned with interconversion between cortisone and cortisol in humans.

5 Claims, 3 Drawing Sheets

OTHER PUBLICATIONS

J. Fain, et al., Effects Of Glucocorticoids On Metabolism Of Adipose Tissue In Vitro, The Journal Of Biological Chemistry (1963) vol. 238, No. 1, p. 54-58.

Pietro Gareri, et al., Antiabsence Effects Of Carbenoxolone In Two Generic Animal Models Of Absence Epilepsy (WAG/Rij rats and lh/lh mice), Neuropharmacology (2005) vol. 49, p. 551-563.

A. Golay, et al., Evolution From Obesity To Diabetes, Diabete & Metabolisme (Paris) (1994): 20, p. 3-14.

J.A. Gomez-Capilla, et al., Effect Of Insulin And Carbenoxolone On Adrenaline Stimulated Lipolysis In Human Lipoma, Horm. Metab. Res. (1990): 22, p. 551-552.

J.A. Gomez-Capilla, et al., Effect Of Carbenoxolone On Glucose Metabolism In Rat Adipose Tissue (1988) vol. 37, No. 7, p. 1299-1301.

Elise P. Gomez-Sanchez, et al., Central Hypertensinogenic Effects Of Glycyrrhizic Acid And Carbenoxolone, Am. J. Physiol (1992): 263, (Endocrinol. Metab. 26) p. E1125-E1130.

Paul Grinberg, et al., Effect Of Metyrapone On Insulin, Cortisol, And Glucose Tolerance Test Responses In Diabetes, New York State Journal Of Medicine (1970) p. 2341-2343.

Muhammad M. Hammami, et al., Regulation Of 11β-Hydroxysteroid Dehydrogenase Activity In Human Skin Fibroblasts: Enzymatic Modulation Of Glucocorticoid Action, Journal of Clinical Endocrinolgy and Metabolism (1991) vol. 73, No. 2, p. 326-334.

H. Hauner, et al., Glucocorticoids And Insulin Promote The Differentiation Of Human Adipocyte Precursor Cells Into Fat Cells, Journal of Clinical Endocrinology and Metabolism (1987), vol. 64, No. 4, p. 832-835.

A. Holmang, et al., The Effects Of Cortisol On Insulin Sensitivity In Muscle, Acta, Physiol Seand (1992): 144, p. 425-431.

B. Jeanrenaud, et al., Studies On Rat Adipose Tissue In Vitro, Journal of Biological Chemistry (1960) vol. 235, No. 8, p. 2217-2223.

W. J. Jeffcoate, et al., Metyrapone In Long-Term Management Of Cushing's Disease, British Medical Journal (1977): 2, p. 215-217.

P. H. Jellinck, et al., Differential Inhibition Of 11β-Hydroxysteroid Dehycrogenase By Carbenolone In Rat Brain Regions And Peripheral Tissues, J. Steroid Biochem. Molec. Biol. (1993) vol. 46, No. 2, p. 209-213.

H. J. Karl, et al., In Vitrol Transformation Of Cortisol By Human Adipose Tissue, Horn. Metab. Res. (1969):1, p. 95.

V. Lakshimi, et al., Regional Distribution Of 11β-Hydroxysteroid Dehydrogenase In Rat Brain, Endocrinology (1991) vol. 128, No. 4, p. 1741-1748.

B. Lambert, et al., Effect of Carbenoxolone On Lipolysis In Rat Adipose Tissue, J. Pharm. Pharmac. (1977): 30, p. 301-303.

Joseph Levin, et al., Extraadrenal Effects Of Metyrapone In Man, Journal Of Clinical Endocrinology And Metabolism (1978) vol. 47, No. 4, p. 845-849.

D. E. W. Livingstone, et al., Is 11β-Hydroxysteroid Dehydrogenase Type 1 A Therapeutic Target? Effects Of Carbenoxolone In Lean And Obese Zucker Rats, Journal Of Pharmacology And Experimental Therapeutics (2003) vol. 305, No. 1, p. 167-172.

P. Loli, et al., Use of Ketoconazole In The Treatment Of Cushing's Syndrome, Journal Of Clinical Endocrinology And Metabolism (1986) vol. 63, No. 6, p. 1365-1371.

Susan C. Low, et al., Glucocorticoids Regulate Hippocampal 11β-Hydroxysteroid Dehydrogenase Activity And Gene Expression In Vivo In The Rat, Journal Of Neuroendocrinology (1994) vol. 6, p. 285-290.

Per Marin, et al., Cortisol Secretion In Relation To Body Fat Distribution In Obese Premenopausal Women, Metabolism (1992) vol. 41, No. 8, p. 882-886.

I. Mineu, et al., Insulinresistance: The Link Between Impaired Glucose Tolerance, Body Mass Index And Plasma Lipids, Rev. Roum. Med. Int. (1993) vol. 31, No. 4, p. 237-243.

M. Moisan, et al., 11β-Hydroxysteroid Dehydrogenase Bioactivity And Messenger RNA Expression In Rat Forebrain: Localization In Hypothalamus, Hippocampus, And Cortex, Endocrinology (1990) vol. 127, No. 3, p. 1450-1455.

C. Monder, et al., 11β-Hydroxysteroid Dehydrogenase, Vitamins and Hormones (1993) vol. 47, p. 187-271.

T. Ohno, et al., Metyrapone-Induced Thermogenesis In Cold And Heat Acclimated Rats, Japanese Journal Of Physiology (1986): 36, p. 821-825.

D. Orth, et al., Hyperfunction, The Adrenal Cortex, p. 536-562.

S. J. Quick, et al., Epithelial And Adipose Cells Isolated From mammary Glands Of Pregnant And Lactating Rats Differ In 11β-Hydroxysteroid Dehydrogenase Activity, J. Steroid Biochem. Molec. Biol. (1990) vol. 37, No. 4, p. 529-534.

S. J. Quick, et al., 11β-Hydroxysteroid Dehydrogenase Activity In The Mammary Gland, J. Steroid Biochem. (1990) vol. 35, No. 6, p. 623-625.

V. Rajan, et al., 11β-Hydroxysteroid Dehydrogenase In Cultured Hippocampal Cells Reactivates Inert 11-Dehydrocorticosterone, Potentiating Neurotoxicity, Journal Of Neuroscience (1996): 16, (1) p. 65-70.

V. Rajan, et al., Cloning, Sequencing And Tissue-Distribution Of Mouse 11β-Hydroxysteroid Dehydrogenase-1 cDNA, J. Steroid Biochem. Molec. Biol. (1995) vol. 52, No. 2, p. 141-147.

P. W. Raven, et al., Extra-Adrenal Effects Of Metyrapone Include Inhibition Of The 11-Oxoreductase Activity Of 11βHydroxysteroid Dehydrogenase: A Model For 11-HSD 1 Deficiency, Clinical Endocrinology (1995) vol. 43, p. 634-644.

R. Sampath-Kumar, et al., Metyrapone Is A Competitive Inhibitor Of 11β-Hydroxysteroid Dehydrogenase Type 1 Reductase, J. Steroid Biochem. Moled. Biol (1997) vol. 62, No. 23, p. 195-199.

Program Abstracts Philadelphia, Endo 2003, Jun. 19-22, 2003. p. 101.

T. C. Sandeep, et al., Increased In Vivo Regeneration Of Cortisol In Adipose Tissue In Human Obesity And Effects Of The 11β-Hydroxysteroid Dehydrogenase Type 1 Inhibitor Carbenoxolone, Diabetes (2005) vol. 54, p. 872-879.

R. M. Sapolsky, et al., Prolonged Glucocorticoid Exposure Reduces Hippocampal Neuron Number: Implications For Aging, Journal Of Neuroscience (1985) vol. 5, No. 5, p. 1222-1227.

R. M. Sapolsky, A Mechanism For glucocorticoid Toxicity In The hippocampus: Increased Neuronal Vulnerability To Metabolic Insults, Journal Of Neuroscience (1985) vol. 5, No. 5, p. 1228-1232.

R. M. Sapolsky, Glucocorticoid Toxicity In The Hippocampus, Neuroendocrinology (1986) vol. 43, p. 440-444.

D. S. Schade, et al., Modulation Of Basal Ketone Body Concentration By Cortisol In Diabetic Man, Journal Of Clinical Endocrinology And Metabolism (1978) vol. 47, No. 3, p. 519-528.

J. R. Seckl, Glycyrrhetinic Acid, An Inhibitor Of 11β-Hydroxysteroid Dehydrogenase, Alters Local Cerebral Glucose Utilization In Vivo, J. Steroid Biochem. Molec. Biol. (1991) vol. 39, No. 5A, p. 777-779.

J. R. Seckl, 11β-Hydroxysteroid Dehydrogenase Isoforms And Their Implications For Blood Pressure Regulation, European Journal Of Clinical Investigation (1993) vol. 23, p. 589-601.

N. Sonino, et al., Ketoconazole Treatment In Cushing's Syndrome: Experience In 34 Patients, Clinical Endocrinolgy (1991) vol. 35, p. 347-352.

P.M. Stewart, et al., Mineralocorticoid Activity Of Carbenoxolone: Contrasting Effects Of Carbenoxolone And Liquorice On 11β-Hydroxysteroid Dehydrogenae Activity In Man, Clinical Science (1990) vol. 78, p. 49-54.

P. M. Stewart, et al., The Cortisol-Cortisone Shuttle And Hypertension, J. Steroid Biochem. Molec. Biol. (1991) vol. 40, No. 4-6, p. 501-509.

B. A. Stein, et al., Chemistry Adrenalectomy Reduces Hippocampal Damage Induced By Kainic Acid, Brain Research (1988) vol. 473, p. 175-180.

A. Tabarin, et al., Use Of Ketoconazole In The Treatment Of Cushing's Disease And Ectopic ACTH Syndrome, Clinical Endocrinology (1991) vol. 34, p. 63-69.

J. Thakore, et al., Cortisol Synthesis Inhibition: A New Treatment Strategy For The Clinical And Endocrine Manifestations Of Depression, Society Of Biological Psychiatry (1995) vol. 37, p. 364-368.

M. Thorén, et al., Aminoglutethimide And Metyrapone In The Management Of Cushing's Syndrome, Acta Endocrinologica (1985) vol. 109, p. 451-457.

J. A. Verheist, et al., Short And Long-Term Responses To Metyrapone in the Medical Management Of 91 Patients With Cushing's Syndrome, Clinical Endocrinology (1991) vol. 35, p. 169-178.

S. M. Virtanen, et al., Dietary Factors In The Aetiology Of Diabetes, Ann. Med. (1994) vol. 26, p. 469-478.

B. R. Walker, et al., Deficient Inactivation Of Cortisol By 11β-Hydroxysteroid Dehydrogenase In Essential Hypertension, Clinical Endocrinology (1993) vol. 39, p. 221-227.

B. R. Walker, et al., Carbenoxolone Increases Hepatic Insulin Sensitivity In Man: A Novel Role For 11-Oxosteroid Reductase In Enhancing Glucocorticoid Receptor Activation, Journal Of Clinical Endocrinology And Metabolism (1995) vol. 80, No. 11, p. 3155-3159.

J. Weidenfeld, et al., In Vitro Metabolism Of Cortisol By Human Abdominal Adipose Tissue, J. Steroid Biochem. (1982) vol. 17, p. 357-360.

O. M. Wolkowitz, Ketoconazole Administration In Hypercortisolemic Depression, Am J. Psychiatry (1993) vol. 150, p. 810-812.

C. De Martinis, Modificazioni Della Tolleranza Al Glucosio Dopo Metopirone In Soggetti Normali E Diabetici Osservazioni Preliminari, Della Societa Italiana Di Biologia Sperimentale (1963) vol. XXXIX, No. 6, p. 372-374.

* cited by examiner

ANOVA: p<0.001
* indicate p<0.05 compared with placebo
NS = not significant

REGULATION OF INTRACELLULAR GLUCOCORTICOID CONCENTRATIONS

REFERENCE TO RELATED APPLICATIONS

This application is a divisional application of allowed U.S. application Ser. No. 09/029,535, filed Feb. 27, 1998 now U.S. Pat. No. 6,368,816, which is the National Stage application of international application PCT/GB96/02134 filed Aug. 28, 1996, published as WO 97/07789 on Mar. 6, 1997, and claims priority from British Application 9517622.8 filed Aug. 29, 1995. Reference is made to U.S. application Ser. No. 10/061,044 filed Jan. 30, 2002 as a divisional application of U.S. application Ser. No. 09/029, 535. Reference is also made to four additional applications, also filed as divisional applications of U.S. application Ser. No. 09/029,535 on Feb. 22, 2002, application numbers to be assigned.

The above-mentioned applications, as well as all documents cited herein and documents referenced or cited in documents cited herein, are hereby incorporated herein by reference.

This invention relates to the interconversion of inactive 11-keto steroids with their active 11β-hydroxy equivalents, to methods by which the conversion of the inactive to the active form may be controlled, and to useful therapeutic effects which may be obtained as a result of such control. More specifically, but not exclusively, the invention is concerned with interconversion between cortisone and cortisol in humans.

Glucocorticoids such as cortisol have a number of diverse effects on different body tissues. For example, the use of cortisol as an anti-inflammatory agent was described in our International Patent Application WO 90/04399, which was concerned with the problem that therapeutically administered cortisol tends to be converted in the body to inactive cortisone by 11β-hydroxysteroid denydrogenase enzymes. Our earlier invention provided for the potentiation of cortisol by the administration of an inhibitor of the 11β-dehydrogenase activity of these enzymes.

Another major physiological effect of cortisol is its antagonism to insulin, and it is known for example that high concentrations of cortisol in the liver substantially reduce insulin sensitivity in that organ, thus tending to increase gluconeogenesis and consequently raising blood sugar levels [1]. This effect is particularly disadvantageous in patients suffering from impaired glucose tolerance or diabetes mellitus, in whom the action of cortisol can serve to exacerbate insulin resistance. Indeed, in Cushing's syndrome, which is caused by excessive circulating concentrations of cortisol, the antagonism of insulin can provoke diabetes mellitus in susceptible individuals [2].

As mentioned above, it is known that cortisol can be converted in the body to cortisone by the 11β-dehydrogenase activity of 11β-hydroxysteroid dehydrogenase enzymes. It is also known that the reverse reaction, converting inactive cortisone to active cortisol, is accomplished in certain organs by 11β-reductase activity of these enzymes. This activity is also known as corticosteroid 11β-reductase, cortisone 11β-reductase, or corticosteroid 11β-oxidoreductase.

It has only recently become apparent that there are at least two distinct isozymes of 11β-hydroxysteroid dehydrogenase (collectively abbreviated as 11β-HSD, which term is used, where appropriate, in this specification). Aldosterone target organs and placenta express a high affinity NAD⁻-dependent enzyme (11β-HSD2)[3]. This has been characterized in placenta and kidney [4,5] and cDNA clones have been isolated [6,9]. 11β-HSD2 catalyses 11β-dehydrogenase activity exclusively [4,7]. In contrast, the previously purified, liver derived isozyme (11β-HSD1) is a lower affinity. NADP⁻/NADPH-dependent enzyme [10,11]. Expression of 11β-HSD1 in a range of cell lines encodes either a bi-directional enzyme [11,12] or a predominant 11β-reductase [13,15] which, far from inactivating glucocorticoids, regenerates active 11β-hydroxysteroid from otherwise inert 11-keto steroid. 11β-reductase activity, best observed in intact cells, activates 11-keto steroid to alter target gene transcription and differentiated cell function [13,14]. 11β-HSD1 and 11β-HSD2 are the products of different genes and share only 20% amino acid homology [6,7].

As far as the applicants are aware no previous attempts have been made to modify the action of 11β-reductase. We have now found that it is possible to inhibit this activity in vivo, and in doing so we have created the possibility of a novel medicament for use in treating many of the deleterious effects of glucocorticoid excess. In one aspect, therefore, the invention provides the use of an inhibitor of 11β-reductase in the manufacture of a medicament for control of 11-keto steroid conversion to 11β-hydroxysteroid in vivo.

As mentioned above, one of the major physiological effects of cortisol is insulin antagonism in the liver, and in a specific aspect the invention therefore provides the use of an inhibitor of 11β-reductase in the manufacture of a medicament for inhibiting hepatic gluconeogenesis [1]. Cortisol promotes hepatic gluconeogenesis by several mechanisms, including antagonism of the effects of insulin on glucose transport, and interactions with insulin and glucose in the regulation of several enzymes which control glycolysis and gluconeogenesis. These include glucokinase. 6-phosphofructokinase, pyruvate kinase, phosphoenolpyruvate carboxykinase (PEPCK), and glucose-6-phosphatase. Inhibiting production of cortisol from cortisone in the liver therefore enhances hepatic glucose uptake and inhibits hepatic glucose production by several mechanisms [16]. Moreover, the influence of inhibiting 11β-reductase activity in the liver of patients with insulin resistance or glucose intolerance may be greater than in healthy subjects because in insulin resistance or deficiency the influence of cortisol on PEPCK has been shown to be great [17]; obese patients secrete more cortisol [18]; insulin resistant patients are more sensitive to glucocorticoids [19]; and insulin down-regulates 11β-HSD1 expression [15,20] so that 11β-reductase activity may be enhanced in conditions of insulin resistance or deficiency.

Our studies have also shown that 11β-HSD1 is expressed in rat adipose tissue and in adipocyte cell lines in culture, where it converts 11-dehydrocorticosterone to corticosterone (the rat equivalents of human cortisone and cortisol, respectively). This suggests that similar 11β-reductase activity will be observed in human adipose tissue, with the result that inhibition of the enzyme will result in alleviation of the effects of insulin resistance in adipose tissue in humans. This would lead to greater tissue utilisation of glucose and fatty acids, thus reducing circulating levels. The invention therefore provides, in a further aspect, the use of an inhibitor of 11β-reductase in the manufacture of a medicament for increasing insulin sensitivity in adipose tissue.

The results of our studies have encouraged us to believe that inhibition of intracellular cortisol production will also lead to increased insulin sensitivity in other tissues which are acted upon by insulin, for instance skeletal muscle [21]. Inhibiting the 11β-reductase therefore promises to reverse the effects of insulin resistance in muscle tissue, and to promote the up-take of essential molecules such as glucose and free fatty acids into muscle cells with consequent improved muscle metabolism and reduction of circulating levels of glucose and fatty acids. In a further aspect, the invention therefore provides the use of an inhibitor of 11β-reductase in the manufacture of a medicament for increasing insulin sensitivity in skeletal muscle tissue.

It is also known that glucocorticoid excess potentiates the action of certain neurotoxins, which leads to neuronal dysfunction and loss. We have studied the interconversion between 11-dehydrocorticosterone and corticosterone in rat hippocampal cultures, and have found (surprisingly in view of the damaging effects of glucocorticoids) that 11β-reductase activity dominates over 11β-dehydrogenase activity in intact hippocampal cells [22]. The reason for this activity is unknown, but this result indicates that glucocorticoid excess may be controlled in hippocampal cells (and by extension in the nervous system in general) by use of an 11β-reductase inhibitor, and the invention therefore provides in an alternative aspect the use of an inhibitor of 11β-reductase in the manufacture of a medicament for the prevention or reduction of neuronal dysfunction and loss due to glucocorticoid potentiated neurotoxicity. It is also possible that glucocorticoids are involved in the cognitive impairment of ageing with or without neuronal loss and also in dendritic attenuation [23–25]. Furthermore, glucocorticoids have been implicated in the neuronal dysfunction of major depression. Thus, an inhibitor of 11β-reductase could also be of value in these conditions.

It will be appreciated from the foregoing that the potential beneficial effects of inhibitors of 11β-reductase are many and diverse, and it is envisaged that in many cases a combined activity will be demonstrated, tending to relieve the effects of endogenous glucocorticoids in diabetes mellitus, obesity (including centripetal obesity), neuronal loss and the cognitive impairment of old age. Thus, in a further aspect, the invention provides the use of an inhibitor of 11β-reductase in the manufacture of a medicament for producing multiple therapeutic effects in a patient to whom the medicament is administered, said therapeutic effects including an inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

From an alternative point of view, the invention provides a method of treatment of a human or animal patient suffering from a condition selected from the group consisting of hepatic insulin resistance, adipose tissue insulin resistance, muscle insulin resistance, neuronal loss or dysfunction due to glucocorticoid potentiated neurotoxicity, and any combination of the aforementioned conditions, the method comprising the step of administering to said patient a medicament comprising a pharmaceutically active amount of an inhibitor of 11β-reductase.

As mentioned previously, the factors which control the relative activities of 11β-dehydrogenase and 11β-reductase in different conditions, especially by the 11β-HSD1 isozyme are poorly understood. It is likely that an 11β-reductase inhibitor will be selective for the 11β-HSD1 isozyme in vivo. We have found, for instance, that glycyrrhetinic acid (a known inhibitor of 11β-dehydrogenase) has no effect on 11β-reductase in vivo [26]. However, we have surprisingly found that carbenoxolone, which is known as an inhibitor of the 11β-dehydrogenase enzyme, also inhibits 11β-reductase in vivo [26,27]. In preferred embodiments, therefore, the inhibitor is carbenoxolone (3β-(3-carboxyproprionyloxy)-11-oxo-olean-2-en 30-oic acid), or a pharmaceutically acceptable salt thereof. The dose of carbenoxolone which we used in our studies was 100 mg every 8 hours given orally.

The invention is hereinafter described in more detail by way of example only, with reference to the following experimental procedures and results and the accompanying figures, in which.

Figure 4:
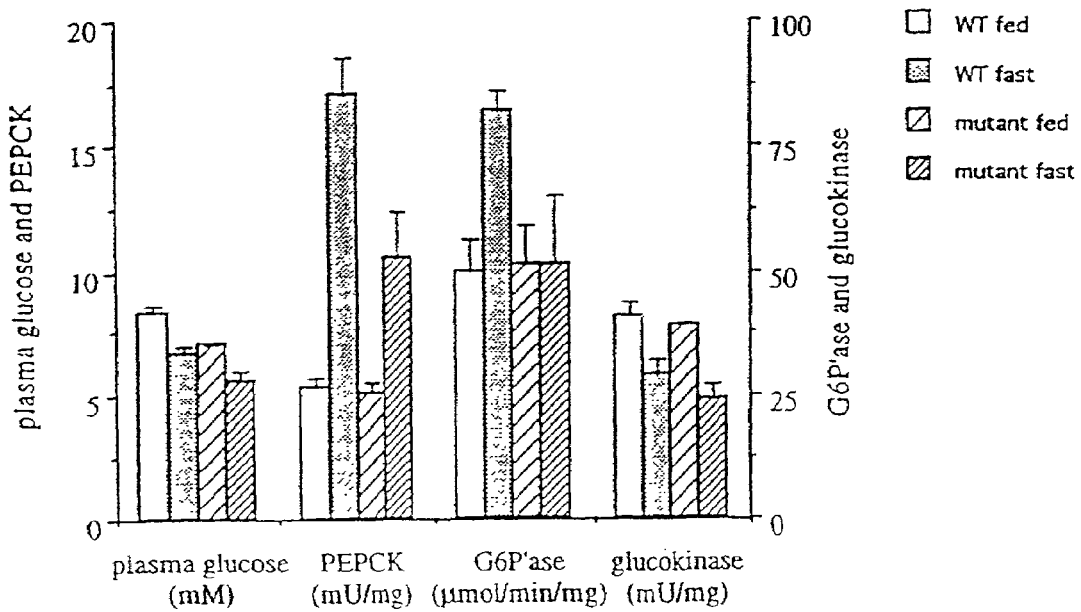
Figure 5:
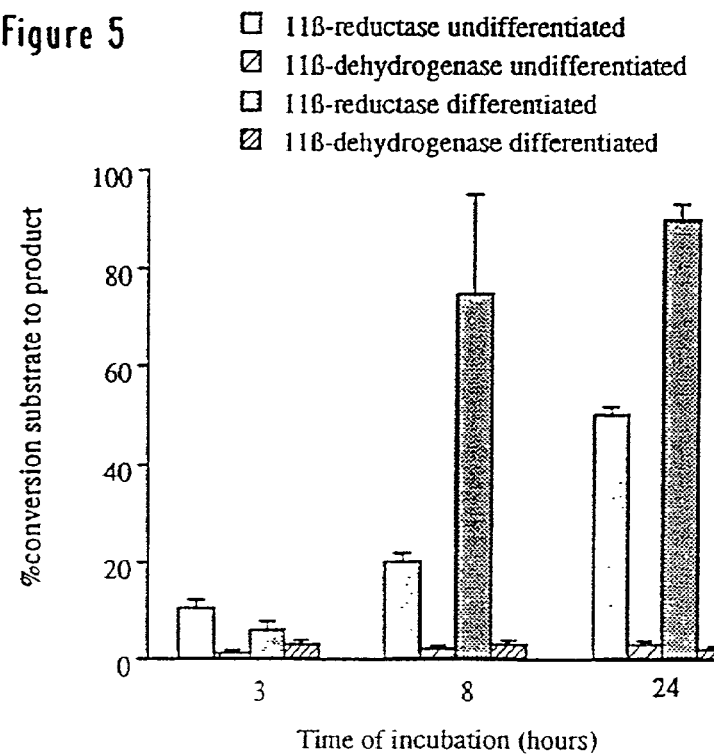
Figure 6:
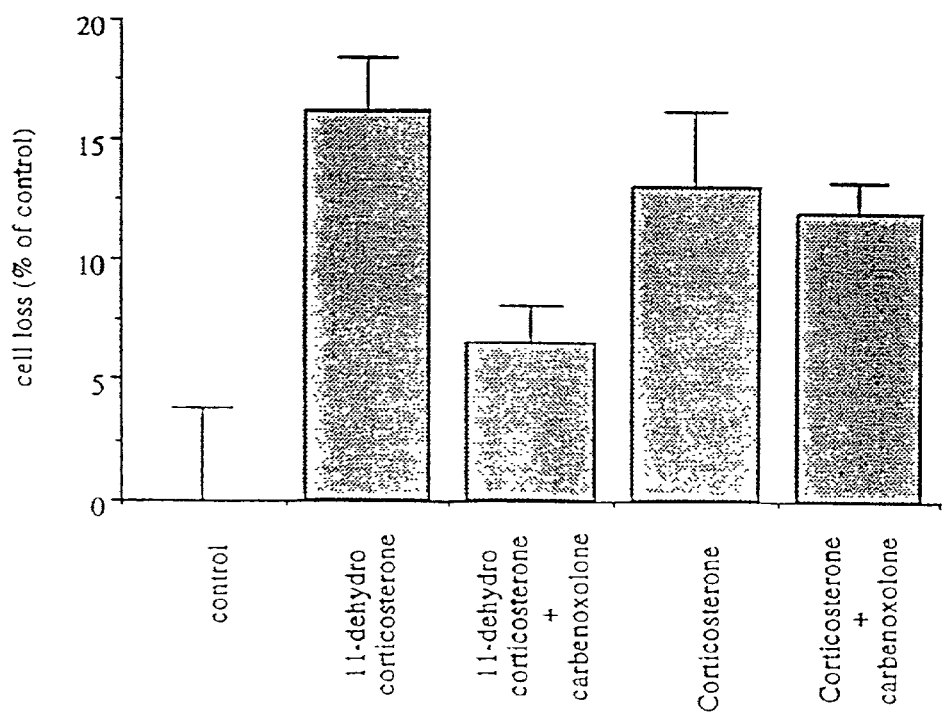

FIG. 4 contains graphs of data obtained from mice which are either homozygous for the wild type 11β-HSD1 allele or which are homozygous for a knockout mutant allele for 11β-HSD1;

FIG. 5 illustrates 11β-HSD1 enzyme activities and mRNA expression in undifferentiated and differentiated 3T3-F442A cells;

FIG. 6 is a graph illustrating the effect of pretreatment with corticosterone and 11-dehydrocorticosterone with or without carbenoxolone, upon rat hippocampal cell survival on exposure to kainic acid.

EXPERIMENTAL RESULTS IN SUPPORT OF THE INVENTION

A. Insulin Sensitivity

A.1 Effect of Carbenoxolone on Insulin Sensitivity in Man

Consistent with the observations in animal tissues and cultured cells described above, we have established the relative activities of 11β-dehydrogenase and 11β-reductase in vivo in different organs in man by measuring the cortisol/cortisone ratio in plasma from selective venous catheterisations [28]. In most organs the venous effluent contains cortisol and cortisone in a ratio of ~10:1. However, in renal vein plasma the ratio is 3:1, while in hepatic vein plasma the ratio is 55:1, consistent with potent 11β-dehydrogenase activity due to 11β-HSD2 expression in the kidney and potent 11β-reductase 11β-HSD1 activity in the liver. Moreover, cortisone taken orally, and therefore delivered to the liver via the portal vein, is avidly converted on first pass to cortisol in the peripheral circulation [26,27]. Using this index of 11β-reductase activity we have shown that, in addition to inhibiting renal 11β-dehydrogenase activity, carbenoxolone (but not glycyrrhetinic acid) [26,27] inhibits hepatic 11β-reductase activity in vivo in man.

In the liver, mineralocorticoid receptors are not expressed in significant numbers, but glucocorticoid receptors are abundant. Surprisingly, the affinity of glucocorticoid receptors for cortisol is 10–40 times lower than that of mineralocorticoid receptors [29]. It may be that, by contrast with the protection of high-affinity mineralocorticoid receptors from cortisol required of 11β-dehydrogenase activity in the distal nephron, 11β-reductase activity in the liver is required to ensure that low-affinity glucocorticoid receptors get adequate exposure to cortisol. The free circulating concentrations of cortisol and cortisone are approximately equal, so that a large pool of cortisone is available for activation in the liver. Such a mechanism would be analogous to the intracellular activation of other members of the thyroid-steroid hormone family which circulate in relatively inactive forms [30], such as testosterone which is converted by 5α-reductase to dihydro testosterone, and thyroxine which is converted by 5'-monodeiodinase to tri-iodothyronine.

To test this hypothesis, we have used carbenoxolone to inhibit hepatic 11β-reductase, and observed changes in hepatic glucocorticoid receptor activation inferred indirectly from changes in insulin sensitivity. Hepatic insulin sensitivity decreases and hepatic glucose production increases during both pharmacological [31,32] and physiological [33] increases in glucocorticoid levels. The results of these experiments were published [16] after the filing of our British patent application number 9517622.8 on 29 Aug. 1995.

Methods

Seven non-obese (Body Mass Index<25) healthy male Caucasian volunteers on no medication, aged 27–36 years, were given carbenoxolone (100 mg every 8 hours orally) or matched placebo for seven days in a randomised double-blind cross-over design, with phases separated by at least 4 weeks. On the seventh day of each phase euglycaemic hyperinsulinaemic clamp studies with measurement of forearm glucose uptake were performed, as described in detail in reference 16, the content of which is incorporated herein by reference.

Results

Figure 1:
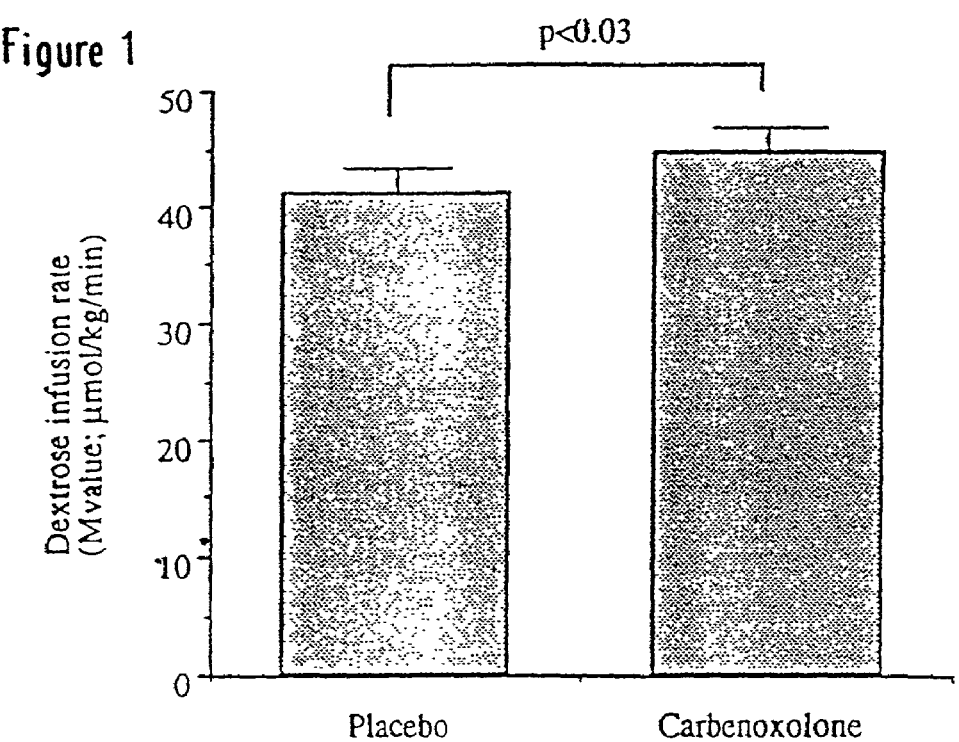
FIG. 1 is a graph showing dextrose infusion rates (M values) after placebo or carbenoxolone administration, in an euglycaemic hyperinsulinaemic clamp study carried out on humans.

Carbenoxolone administration was associated with no change in fasting glucose concentration but a fall in fasting insulin concentration. During the euglycaemic clamp, carbenoxolone enhanced the metabolic clearance rate of glucose (M values 41.1±2.4 μb 5 mol/kg/min for placebo versus 44.6±2.3 for carbenoxolone, p<0.03) (FIG. 1). No difference was detected in peripheral glucose uptake as measured by forearm glucose uptake, but this measurement was less precise due to insulin-induced vasodilatation [34] and the mental stress induced by the restraint of the study conditions.

Discussion

These data show that carbenoxolone increases whole-body insulin sensitivity. This could have resulted from either increased suppression of hepatic glucose production as a reflection of increased hepatic insulin sensitivity, or increased peripheral utilisation of glucose as a reflection of increased peripheral insulin sensitivity. The absence of a change in forearm glucose uptake with carbenoxolone suggests that the former mechanism predominates. However, the imprecision of this measurement raises the possibility that there is a contribution from enhanced peripheral insulin sensitivity which we have not detected. A more detailed discussion of these data has now been published [16].

It is unlikely that carbenoxolone affects insulin sensitivity by a mechanism independent of its effect on 11β-reductase. Carbenoxolone inhibits other enzymes which metabolise cortisol, notably 5β-reductase [35], but this effect would increase intra-hepatic cortisol concentrations and reduce insulin sensitivity. In the absence of corticosteroids, carbenoxolone at this dose has no documented effects in vivo and low affinity for corticosteroids receptors in vitro [36], so that a direct action of carbenoxolone to increase insulin sensitivity is unlikely. Indeed, previous experiments suggest that, at higher concentrations (mmol/l), carbenoxolone without corticosteroid antagonises the action of insulin in adipocytes [37]. Blood pressure and forearm blood flow were not elevated by carbenoxolone in this study, and even if they were this might be associated with reduced insulin sensitivity [34]. Finally, other neurohumoral changes consequent on the renal effects of carbenoxolone (suppressed plasma renin, aldosterone, and potassium concentrations) are not known to influence insulin sensitivity directly, and in the context of oral sodium loading were associated with decreased insulin sensitivity [38].

From these observations we infer that basal 11β-reductase activity plays a role in maintaining adequate exposure of glucocorticoid receptors to cortisol in human liver. The circulating pool of cortisone is therefore physiologically important as a source of active glucocorticoid in sites where 11β-reductase is expressed.

A.2 Effect of Carbenoxolone on Insulin Sensitivity in the Rat

Following our studies of the effects of carbenoxolone in healthy humans, we have performed unpublished studies of the effects of carbenoxolone in intact healthy rats. Consistent with the observations in human, we have shown that rat hepatocytes in primary culture express 11β-HSD1 which has predominant 11β-reductase activity [15]. We have also shown that the circulating concentration of 11-dehydrocorticosterone (measured by gas chromatography and mass spectrometry) is 40–50 nmol/l (Dr. R. Best, unpublished observation) so that there is a substantial pool of inactive 11-ketosteroid available for activation to corticosterone in sites where 11β-reductase is active.

Methods

Intact male Wistar Hans rats of body weight 200–250 g were treated with daily subcutaneous injection of 1 ml of either 0.9% saline (vehicle) or carbenoxolone (made up to 1,3 or 10 mg/ml in 0.9% saline) for 14 days. They were fasted from 4 pm and blood obtained by tail-nick at 9 am the next day. Plasma glucose was measured by a glucose oxidase method on a Beckman CX-3 autoanalyser.

Results

Figure 2:
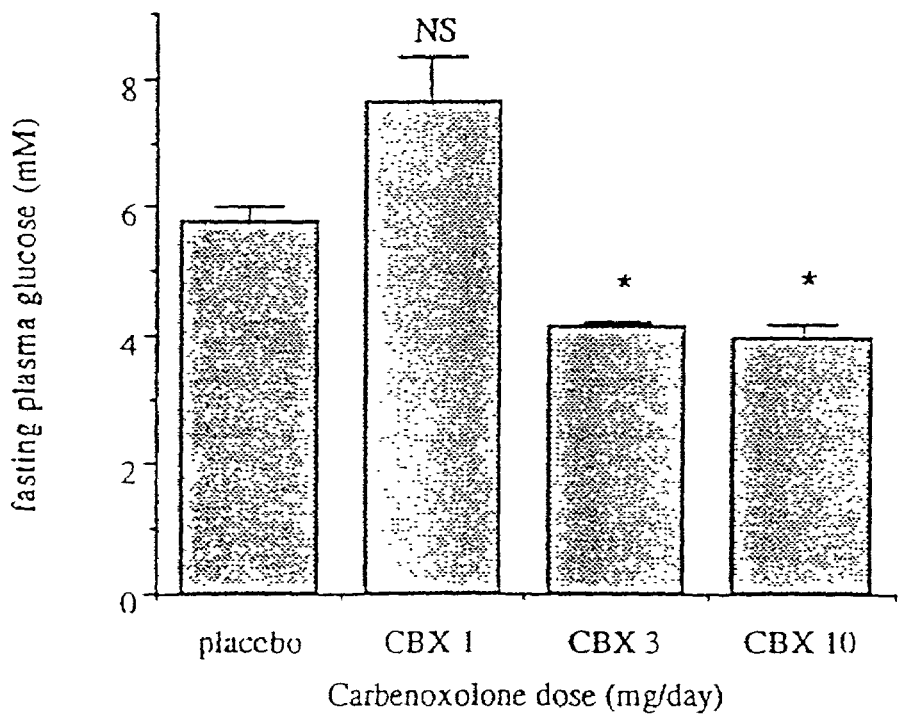
FIG. 2 is a graph showing fasting plasma glucose concentration in rats after placebo or carbenoxolone therapy at the daily doses indicated.

Carbenoxolone produced a dose-dependent fall in tasting glucose concentrations (FIG. 2).

Discussion

These experiments are preliminary, since it is now our intention to assess insulin sensitivity and glucose tolerance in rats treated with carbenoxolone. However, the fall in fasting plasma glucose is consistent with inhibition of hepatic gluconeogenesis with or without enhanced peripheral glucose uptake in rats treated with the 11β-reductase inhibitor carbenoxolone.

A.3 Effect of Estradiol-mediated Inhibition of Hepatic 11β-HSD1 Expression on Insulin Sensitivity in the Rat Having established the effects of a competitive pharmacological inhibitor of 11β-reductase activity on insulin sensitivity and glucose levels in man and rat, the object of this study was to examine the effects of down-regulation of transcription and translation of the 11β-HSD1 enzyme. The results of these studies have been presented at scientific meetings during 1996 but are not yet published.

11β-HSD1 expression is regulated by a variety of hormones in vivo [26]. In the rat liver, 11β-HSD1 shows pronounced sexual dimorphism, with lower activity in females. Indeed, chronic estradiol administration almost completely suppresses hepatic 11β-HSD1 expression in both male and female rats [39–41]. This regulation appears to be tissue- and isozyme-specific, as estrogen does not attenuate 11β-HSD1 expression in the hippocampus or 11β-HSD2 activity in the kidney [41]. The aim of this study was therefore to examine the contribution which reactivation of glucocorticoids by hepatic 11β-HSD1 makes to the expression of liver-specific glucocorticoid modulated genes in the rat by exploiting the selective suppression of hepatic 11β-HSD1 by estradiol in vivo.

Methods

In-vivo Studies

Male Han Wistar rats (200–250 g) underwent gonadectomy and either bilateral adrenalectomy of sham-operation under halothane anaesthesia. For estradiol administration, silicone elastomer capsules (1.95 mm internal diameter, 3.125 mm external diameter). (Dow Corning Corporation, Midland, Mich., U.S.A.) containing 17β-estradiol (Sigma, Poole, UK) were implanted subcutaneously. For animals treated for 42 days with estradiol, the capsules were removed and replaced after 21 days. Control animals were implanted with blank capsules. Adrenalectomised rats were maintained on 0.9% saline. Rats were killed 10, 21 or 42 days after surgery. Liver and hippocampus were removed and dissected on ice for assay of 11β-HSD activity and an aliquot of liver was frozen on dry ice and stored at −80° C. until extraction of RNA.

Quantitation of 11β-HSD Activity in In Vivo Experiments

Tissues were homogenised in Krebs-Ringer bicarbonate buffer with 0.2% glucose, pH 7.4, and assayed as described previously [40]. Homogenates (6.25 μg of liver protein, 250 μg of hippocampal protein) were incubated with 200 μM NADP (Sigma, Poole, UK) and 12 nM [$^3$H]-corticosterone (specific activity 84 Ci/mmol; Amersham International, Aylesbury, UK) in a total volume of 250 μl with Krebs-Ringer buffer supplemented with 0.2% bovine serum albumin for 10 min at 37° C. 11β-dehydrogenase activity was quantified in this assay as a measure of active enzyme since 11β-reductase is unstable in homogenates. Steroids were extracted with ethyl acetate and separated by HPLC with on-line β counter. 11β-HSD activity was expressed as conversion of corticosterone to 11-dehydrocorticosterone, after correction for apparent conversion in incubates without enzyme (<3%)

Extraction and Analysis of mRNA

Total RNA was extracted from liver tissue by the guanidinium thiocyanate method, as described [40] and resuspended in diethylpyrocarbonate-treated water. RNA concentration and purity was assayed spectrophotometrically 20 μg aliquots were separated on a 1.2% agarose gel containing 2% formaldehyde. RNA was blotted onto nitrocellulose membranes (Hybond-N, Amersham International, UK), pre-hybridized in 6 ml phosphate buffer (0.2 M NaH$_2$PO$_4$, 0.6 M NaH$_2$PO$_4$, 5 mM EDTA). 3 ml 20% SDS and 100 μg denatured herring testis DNA (Sigma, Poole, UK) for 2 h at 55° C. and hybridized at 55° C. overnight in the same solution containing rat 11β-HSD1 or PEPCK cDNA, labelled with $^{32}$P-dCTP using a random primed DNA labelling kit (Boehringer Mannheim UK Ltd., Lewes, UK). Three 20 min washes were carried out at room temperature in 1×SSC (0.3 M NaCl, 0.03 M sodium citrate), 0.1% SDS followed by a stringent wash at 55° C. for 30 min in 0.3×SSC, 0.1% SDS. Filters were exposed to autoradiographic film for 1–4 days (adjusted to ensure the signal density was within the linear range). Filters were rehybridised with similarly labelled 7S cDNA or transferrin RNA cDNA probes to control for loading, as previously described [40] (transferrin mRNA expression is not altered by estradiol or glucocorticoid). Optical density was determined using a computer-driven image analysis system (Seescan plc, Camps, UK). Values were expressed as a percentage of control levels.

Statistics

Data are the means±SEM of 5–10 replicates (indicated in figure legends). Data were compared by ANOVA and Newman-Keuls post-hoc test or by Student's unpaired t-test, as appropriate. Statistical tests were carried out on absolute data, but the figures display data as percent of values for control animals to improve clarity.

Results

Effect of Chronic Estradiol Treatment on 11β-HSD1 Activity and mRNA Expression

Figure 3:
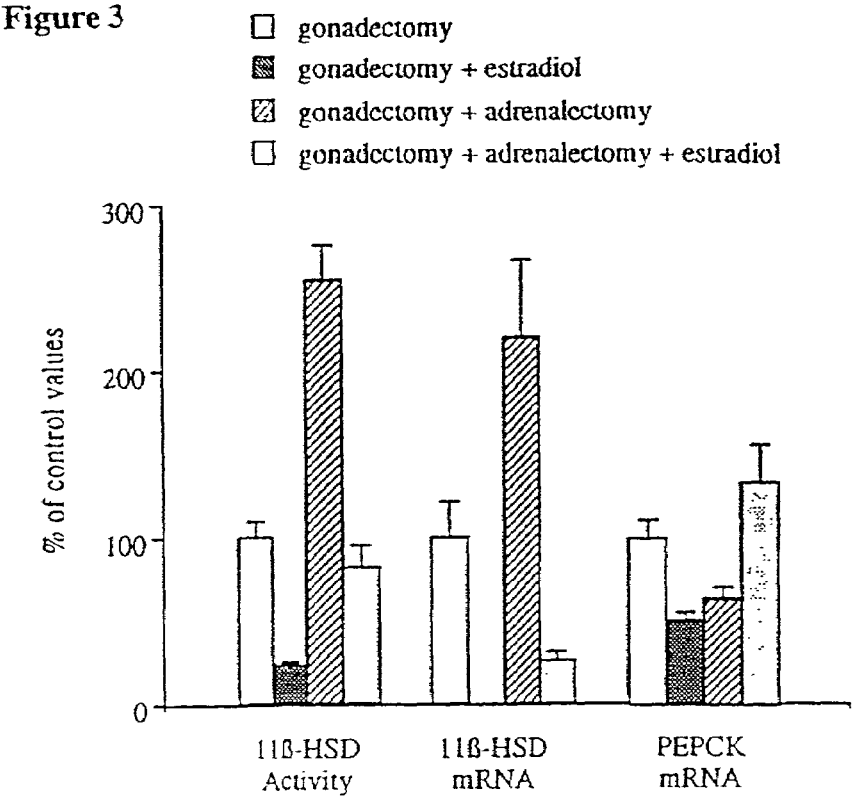
FIG. 3 is a graph illustrating the effect of estradiol administration to gonadectomised or gonadectomised/adrenalectomised rats on hepatic 11β-HSD1 activity, and mRNA expression for 11β-HSD1 and PEPCK.

Estradiol administration for 10, 21 and 42 days to gonadectomised male rats resulted in marked decreases in hepatic 11β-HSD activity (FIG. 3). However, 11β-HSD activity was not completely abolished since prolonged (60 min) incubation of liver homogenates from rats given estradiol for 42 days showed detectable (12.2±14.7%) conversion of corticosterone to 11-dehydrocorticosterone 11β-HSD1 mRNA expression fell to undetectable levels after 21 and 42 days of estradiol treatment. 11β-HSD activity in the hippocampus was not altered by estradiol treatment at 21 or 42 days (data not shown).

Effect of Estradiol on Hepatic Glucocorticoid-inducible Gene Expression

To examine the effect of attenuated hepatic 11β-HSD1 activity on local glucocorticoid action, the expression of liver-specific glucocorticoid-inducible genes was measured after 42 days of estradiol. PEPCK mRNA expression was significantly reduced by estradiol treatment (FIG. 3).

To examine whether these effects of estradiol on hepatic gene expression were mediated directly or via alterations in glucocorticoid action in the liver, the effects of estradiol in adrenalectomised animals or sham-operated controls was examined. Animals were killed after 21 days. Plasma corticosterone values confirmed the adequacy of adrenalectomy (data not shown). Adrenalectomy increased hepatic 11β-HSD1 gene expression and activity compared with sham-operated controls (FIG. 3). Estradiol reduced liver 11β-HSD1 mRNA and activity in adrenalectomised rats, and although mRNA expression was higher than estradiol-treated adrenally-intact rats, it remained significantly reduced compared with untreated controls.

Hepatic PEPCK gene expression was decreased after 21 days of estradiol treatment, albeit to a slightly lesser extent than after 42 days (FIG. 3). Unsurprisingly, adrenalectomy also attenuated hepatic PEPCK gene expression, but in adrenalectomised rats estradiol no longer reduced, but indeed increased PEPCK mRNA levels when compared with adrenalectomy alone.

Discussion

Estradiol administration for both 21 and 42 days produced undetectable hepatic 11β-HSD1 mRNA expression and markedly reduced 11β-HSD activity (although this remained clearly measurable), confirming previous studies [41]. The discrepancy between mRNA expression and activity might be due to much slower turnover of 11β-HSD1 protein or, more likely, to the transcription and translation of residual low levels of 11β-HSD1 mRNA, undetectable by northern analysis. This effect of sex steroids is relatively specific to the liver, since hippocampal 11β-HSD1 was unaffected, and previous studies have shown that 11β-HSD2 is not attenuated by estrogens [22]. Thus the advantage of exploiting estrogen down-regulation of hepatic 11β-HSD1, as opposed to conventional carbenoxolone or other inhibitors of the enzyme, is that 11β-HSD2 is unaffected.

Following 42 days of estradiol treatment, hepatic expression of mRNA encoding PEPCK was clearly reduced. In principle, this effect of chronic estrogen treatment may be explained in several ways: (i) estrogen may act directly to repress hepatic gene expression; (ii) estradiol may alter corticosteroid metabolism in the liver. Reduced hepatic 11β-HSD1-mediated reactivation of otherwise inert 11-dehydrocorticosterone is anticipated to reduce expression of these glucocorticoid-sensitive transcripts; (iii) there may be other indirect effects of chronic estradiol administration.

For PEPCK direct inhibition by estradiol appears unlikely, since this transcript was induced by estrogen in adrenalectomised rats. The loss of the attenuating effect of estradiol on PEPCK expression in adrenalectomised rats suggests a requirement for glucocorticoids in the process, rather than any other indirect effect. Glucocorticoids increase expression of PEPCK in the liver [17] and so this pattern of changes is compatible with the glucocorticoid control of expression of this gene. The effect of estradiol in intact rats was as potent as adrenalectomy alone in attenuating PEPCK mRNA expression. These data are therefore consistent with the effects of estradiol being indirectly mediated via the marked loss of 11β-HSD1 11β-reductase activity, which thus attenuates intrahepatic glucocorticoid regeneration. Thus the 11β-reductase activity of 11β-HSD1 is likely to be of key importance in producing sufficiently high intrahepatic corticosterone levels to elevate PEPCK above the minimum levels maintained by basal (non-glucocorticoid) factors.

A.4 Effect of Transgenic Knockout of 11β-HSD1 Expression

Although the effects of carbenoxolone and estrogen-induced downregulation of 11β-HSD1 expression provide strong support for our hypothesis that 11β-reductase inhibition will enhance insulin sensitivity and reduce hepatic glucose production, both of these agents are potentially confounded by other actions, including direct effects on 11β-HSD2 (carbenoxolone) and other effects on the liver (estrogen). The most clear-cut evidence of the importance of a specific protein can now be tested most effectively using transgenic technology. We have now produced a transgenic mouse which is homozygous for a mutant allele carrying a targetted disruption of the 11β-HSD1 gene. Some of these results have been presented at scientific meetings during 1996 but have not yet been published.

Methods

A mouse genomic library constructed from isogenic OLA129 DNA in the lambda vector GEM12 was screened with a rat 11β-HSD1 cDNA probe. A lambda phage containing a 14 kb insert encompassing exons 2 to 5 of the mouse 11β-HSD1 gene was cloned and subjected to extensive restriction mapping and sequence analysis. Using this information, a replacement vector 16 KpnβA was constructed using the pBS-KpnA cassette. The vector consisted of the neomycin resistance gene under the control of the human β-actin promoter and followed by the SV40 polyadenylation signal. The 6.5 kb long 3' homology arm was subcloned from intron D. The 1.2 kb short homology arm was synthesised by PCR using high fidelity Ultma Taq polymerase, 129 mouse genomic DNA and primers bearing nested Sac I and Spe I restriction sites and located in exon 1 and intron B. An external probe was synthesised by PCR. Using this probe, a specific recombination event generates a 1.5 kb BamHI fragment instead of a 3 kb fragment expected for the wild type gene.

Following transfection of the 16 kpnβ A replacement construct into 'CGR 8' embryonic stem cells, of 368 neomycin-resistant colonies screened, only one showed homologous recombination at the 5' end. The specificity of the recombination event was tested by Southern blot hybridisation after BamHI restriction. Specificity of restriction at the 3' end was also confirmed by hybridisation with an internal probe after three different restrictions.

Positive embryonic stem cells were injected into C57B1/6 blastocysts to generate chimeric offspring who were cross-bred to establish a colony of homozygotes for the knockout allele.

Results

Homozygotes for the mutant allele are morphologically intact and fully fertile. No survival bias is conferred by the mutant allele. However, neither 11β-HSD1 mRNA nor enzyme activity (techniques as above) were detected in mutant homozygotes, and reduced mRNA and activity were detected in heterozygotes. Plasma corticosterone levels are not altered in mutants, but the ratio of corticosterone to 11-dehydrocorticosterone in urine is markedly reduced. Homozygous mutant mice are also unable to convert 11-dehydrocorticosterone to corticosterone in vivo and are thus resistant to the thymic involution seen with 11-dehydrocorticosterone in wild-type control mice.

Animals were fasted for 48 hours before sacrifice and collection of trunk blood. Plasma glucose was measured by a glucose oxidase method (see above). Fasting plasma glucose concentrations were lower in mutant animals (FIG. 4).

Measurement of enzymes responsible for hepatic glycolysis/gluconeogenesis revealed no difference between wild type and mutant animals in the fed state. However, on fasting the mutant animals failed to show the normal induction of glucose-6-phosphatase and PEPCK (FIG. 4). Glucokinase was not altered.

Discussion

These data demonstrate the importance of 11β-HSD1 in hepatic glucose metabolism and insulin sensitivity. Glucose-6-phosphatase and PEPCK are two gluconeogenic enzymes which are down-regulated by insulin and up-regulated by glucocorticoid exposure [1]. In the presence of insulin (in fed animals) there is no change in expression of these enzymes, confirming that insulin regulation is dominant. However, in starved animals with low insulin levels there is a failure of induction of these enzymes consistent with a failure of corticosterone-dependent induction. In animals in which the mutant vector has recombined specifically to knockout only 11β-HSD1, and in which plasma corticosterone is maintained by normal hypothalamic-pituitary-adrenal feedback these changes can be attributed to impaired intrahepatic conversion of 11-dehydrocorticosterone to corticosterone.

A.5 Role of 11β-HSD1 in Adipocyte Maturation

Glucocorticoids are involved in triggering adipocyte differentiation from uncommitted adipoblasts into committed preadipocytes. Glucocorticoid excess in humans causes profound changes in both adipose tissue distribution and metabolism [18]. In Cushing's syndrome, omental fat shows adipose cell hyperplasia, associated with enhanced lipoprotein lipase and glycero-phosphate dehydrogenase activity in homogenised adipose tissue cortisol and corticosterone are oxidised to cortisone and 11-dehydrocorticosterone, indicating the presence of 11β-HSD [42] which might modify glucocorticoid action in a sites- and developmentally-specific manner. We have (i) examined the expression of 11β-HSD enzyme activity and 11β-HS1 and mRNA in isolated primary rat adipocytes; and (ii) determined whether 11β-HSD1 is expressed in a fibroblast derived clonal cell line. 3T3-F442A which can be induced into mature adipocytes in presence of fetal calf serum and insulin. The results of this work have not been published.

Methods

Animals

Epididymal adipose tissue was excised from adult male Wistar rats. Adipose tissue was washed several times in Phosphate Buffered Saline, trimmed of large blood vessels and minced. Tissue was incubated in Krebs-Ringer buffer (KRB) containing collagenase II (2 mg/ml) (Sigma, UK) at 37° C. for 40 min, and the digested material passed through a 250 µm nylon filter and briefly centrifuged. The separated adipocyte (floating) and stromal vascular (pellet) fractions were collected for (i) RNA extraction and northern blot as described above and (ii) 11β-dehydrogenase bioactivity assay as described above, using final concentrations of 500 µg protein/ml. 200 µM cofactor (NADP or NAD), and 12 nM 1, 2, 6, 7-$^3$H-corticosterone in a total volume of 250 µl Krebs-Ringer buffer for 15 min at 37° C.

Cell Culture

Clonal preadipocyte cell lines 3T3-F442A, (kindly provided by Dr. Pairault Henri Modor Hospital, Creteil, France) were plated at a density of $10^4$ cells/100 mm diameter dishes in 'basal medium' (Dulbecco's modified Eagle's medium (DMEM), supplemented with 10% newborn calf serum, penicillin 200 U/ml and streptomycin 50 µg/ml). To differentiate confluent 3T3-F442A cells, basal medium was replaced with 'differentiation medium' (DMEM, 10% fetal calf serum and insulin, 5 µg/ml) and maintained in this for 11 days with the medium changed every 48 h.

11β-Dehydrogenase and 11β-reductase activities were measured in intact cells by addition of 25 nM corticosterone with labelled $^3$H-corticosterone or 25 nM 11-dehydrocorticosterone with labelled $^3$H-11-dehydrocorticosterone. Interconversion of corticosterone and 11-dehydrocorticosterone was assessed as above at 3, 8 and 24 h after the addition of steroids.

Results

Extracts from homogenized rat adipocytes showed 11β-HSD activity, as demonstrated by conversion of corticosterone to 11-dehydrocorticosterone. 11β-HSD1 was transcribed in whole white adipose tissue and isolated adipocytes as a single, approximately 1.6 kb species of mRNA, of similar size to the hepatic species, though expression was lower than in liver 11β-HSD1 transcripts were also expressed in the stromal vascular fraction (data not shown).

3T3-F442A cells were induced to differentiate and after 10 days, >90% cells were differentiated as determined by visible lipid accumulation. Associated with this differentiation there was a marked increase in 11β-HSD1 mRNA expression and 11β-reductase activity which occurred late (8 days after addition of differentiation medium) and in association with induction of GPDH expression (FIG. 5).

Discussion

In this study, we have demonstrated 11β-HSD1 gene expression in rat adipose tissue and isolated rat adipocytes, as well as the stromal vascular preadipocyte fraction, in agreement with data demonstrating 11β-HSD activity in the adipose component of the mammary gland [42]. By contrast with data obtained in homogenised tissue and in keeping with findings in other whole cell preparations [15, 22], we have found in whole cells that 11β-HSD1 operates as an 11β-reductase rather than 11β-dehydrogenase enzyme in addition, in the 3T3-F442A cell line, we have demonstrated that 11β-HSD1 expression is regulated in a differentiation-dependent manner. 11β-HSD1 thus has the characteristics of a 'late' differentiation gene. Moreover, the regulated expression of 11β-HSD1 paralleled that of GPDH, a glucocorticoid-sensitive late marker of adipocyte differentiation.

These results support the hypothesis that 11β-reductase plays a physiological role in converting 11-keto steroids to 11β-hydroxy steroids and thus amplifying glucocorticoid activity. In the adipocyte this may explain the induction of GPDH. Although inhibition of 11β-reductase would not be expected to influence the early differentiation of adipocytes, it may influence the biochemical phenotype of differentiated cells, specifically in relation to lipid metabolism.

B Neuronal Effects of 11β-Reductase Inhibitors

Several studies have demonstrated 11β-HSD activity, immunoreactivity and mRNA expression in hippocampal neurons [43]45. Administration of 11β-HSD inhibitors alters functional activity in the hippocampus in vivo [46], although the mechanisms underpinning this effect are obscure.

Previous studies have shown that in homogenates of hippocampus, both dehydrogenation and reduction occur [44], but the reaction direction in intact cells was previously unknown. We have now examined 11β-HSD activity and its function in primary cultures of fetal hippocampus cells. The results of these experiments were published [22] after the filling of our patent application No. 9517622.8 on 29 Aug. 1995. Further details of the experiments will be found in reference 22, the contents of which are incorporated herein by way of reference.

Methods and Results

Hippocampi were dissected from Wistar rat embryos on day 18.5 of pregnancy and cultured in DMEM with supplements, as described [22]. These cells expressed 11β-HSD1 mRNA, and homogenised cells performed either 11β-dehydrogenase or 11β-reductase activity. However, in whole cells in culture, only 11β-reductase activity was demonstrated. This 11β-reductase activity could be almost abolished by the addition of carbenoxolone ($10^{-6}$M) [22].

To assess the influence of 11β-reductase activity on neurotoxicity, cells were exposed to kainic acid and cell survival determined. Both corticosterone and 11-dehydrocorticosterone potentiated kainic acid neurotoxicity. However, carbenoxolone did not alter the effect of corticosterone, but protected the cells from the potentiating effect of 11-dehydrocorticosterone (FIG. 6).

Discussion

These data demonstrate that 11β-HSD1 is an 11β-reductase enzyme in rat hippocampus and that the conversion of 11-ketosteroids to 11-hydroxysteroids potentiates the neurotoxic action of glucocorticoids. Importantly, they show that inhibition of 11β-reductase activity can protect the cells from the damage that occurs due to reactivation of 11-dehydrocorticosterone. This supports the hypothesis that inhibition of 11β-reductase in human brain would prevent reactivation of cortisone into cortisol and protect against deleterious glucocorticoid-mediated effects on neuronal survival and other aspects of neuronal function, including cognitive impairment, depression, and increased appetite.

REFERENCES

1. Dallman M F, Strack A M, Akana S F, et al Front Neuroendocrinol 14, 303–347 (1993).
2. Ross E J & Linch D C, Lancet 2, 646–649 (1982).
3. Walker B R, Campbell J C, Williams C R W Endocrinology 131, 970–972 (1992).
4. Brown R W, Chapman K E, Edwards C R W & Seckl J R Endocrinol 132, 2614–2621 (1993).
5. Rusvai E & Náray-Fejes-Tóth A J Biol Chem 268, 10717–10720 (1993).

6. Agarwal A K. Mune T. Monder C & White P C (1994) J Biol Chem 269, 25959–25962 (1994).
7. Albiston A L, Obeyesekers V R, Smith R E & Krozowski Z S Mol Cell Endocrinol 105, R11–R17 (1994).
8. Náray-Fejes-Téch A & Fejes-Tóth G. Endocrinology 136, 2579–2586 (1995).
9. Brown R W, Chapman K E, Koteletsev Y. et al. Biochem J 313, 1007–1017 (1996).
10. Lakshmi V & Monder C Endocrinol 123, 2390–2398 (1988).
11. Agarwal A K, Monder C. Eckstein B & White P C J Biol Chem 254, 18939–18943 (1989).
12. Agarwal A K, Tusie-Luna M-T, Monder C & White P C Mol Endocrinol 4, 1827–1832 (1990).
13. Duperrex H, Kenouch S, Gaeggleler H P, et al. Endocrinology 132, 612–619 (1993).
14. Low S C, Chapman K E, Edwards C R W & Seckl J R Journal of Molecular Endocrinology 13, 167–174 (1994).
15. Jamieson P M, Chapman K E, Edwards C R W & Seckl J R. Endocrinology 136, 4754–4761 (1995).
16. Walker B R, Connacher A A , Lindsay R M, Webb D J & Edwards C R W, J Clin Endorcinol Metab 80, 3155–3159 (1995).
17. Friedman J E, Yun J S, Patel Y M, McGrane M M & Hanson R W J. Biol Chem 368, 12952–12957 (1993).
18. Bjorntorp P. J Intern Med 230, 195–201 (1991).
19. Walker B R, Seckl J R & Phillips D I W. J. Endocrinol 148(suppl), P370 (1996). (Abstract)
20. Hammami M M & Siiteri P K. J Clin Endocrinol Metab 73, 326–334 (1991).
21. Monder C & Shackleton C H L. Steroids 44, 383–417 (1984).
22. Rajan V, Edwards C R W & Seckl J R. J Neurosci 16, 65–70 (1996).
23. Landfield P W, Waymire J & Lynch G Science 202, 1098–1102 (1978).
24. Sapolsky R M, Krey L C & McEwen B S J Neurosci 5, 1221–1226 (1985).
25. Sapolsky R M, Krey L C & McEwen B S Endocr Rev 7, 284–301 (1986).
26. Walker B R, Edwards C R W. Endocrinol Metal Clin N Amer. 23(2), 359–377 (1994).
27. Stewart P M, Wallace A M, Atherden S M, Shearing C H, Edwards C R W Clin Sci 78, 49–54 (1990).
28. Walker B R, Campbell J C, Fraser R, Stewart P M, Edwards C R W Clin Endocrinol (Oxf) 27, 483–492 (1992).
29. Arriza J L, Weinberger C, Cerelli G Science 237, 268–275 (1987).
30. Stewart P M & Sheppard M C Mol Cell Endocrinol 83, C13–18 (1992).
31. de Feo P, Perriello C, Torlone E, et al Am J Physiol 257, E35–E42 (1989).
32. Rooney D P, Neely R D G, Cullen C, Ennis C N, Sheridan B, Atkinson A B. J Clin Endocrinol Metab 77, 1180–1183 (1994).
33. Dinneen S, Alzaid A, Miles J, Rizza R J Clin Invest 92, 2283–2290 (1993).
34. Tappy L, Randin D, Vollenweider P, et al. J Clin Endocrinol Metab 79, 1063–1069 (1994).
35. Latif S A, Conca T J, Morris D J Steroids. 55 , 52–58 (1990).
36. Armanini D, Karbowiak I, Funder J W Clin Endocrinol (Oxf). 19, 609–612 (1983).
37. Gomez-Capilla J A, Gutierrez C, Fernandez-Fernandez J M Biochem Pharmacol 37, 1299–1301 (1988).
38. Donovan D S, Solomon C G, Seely E W, Williams G H, Simonson D C Am J Physiol 264, E730–E734 (1993)
39. Lax E R, Ghraf R & Schriefers E Acta Endocrinol (Copenh) 89, 352–358 (1978).
40. Low S C, Moisan M-P, Edwards C R W & Seckl J R J Neuroendocrinol 6, 285–290 (1994) .
41. Low S C, Chapman K E, Edwards C R W Wells T, Robinson I C A F & Seckl J R J Endocrinol 143, 541–548 (1994).
42. Quirk S J, Slattery J & Funder J W J Steroid Biochem 35, 623–625 (1990).
43. Moisan M -P, Seckl J R & Edwards C R W Endocrinol 122, 1450–1455 (1990).
44. Lakshmi V, Seckl P R, McEwen B S & Monder C Endocrinol 128, 1741–1748 (1991).
45. Sakai R R, Lakshmi V, Monder C & McEwen B S J Neuroendocrinol 4, 101–106 (1992).
46. Seckl J R, Dow R C, Low S C, Edwards C R W & Fink G. J Endocrinol 136, 471–477 (1993).

The invention claimed is:

1. A method for reducing circulating fatty acids in adipose tissue in a patient in need thereof comprising
   determining reductase activity of 11-Beta-hydroxysteroid dehydrogenase 1 (11 Beta HSD1) in adipose tissue,
   determining whether a compound or composition inhibits said reductase activity of 11 Beta HSD1 in adipose tissue, and
   administering to said patient said compound or composition which inhibits said reductase activity of 11-Beta HSD1 in adipose tissue, in an amount effective to so inhibit said reductase activity of 11-Beta HSD1 in adipose tissue.

2. The method of claim 1, wherein determining whether a compound or composition inhibits said reductase activity of 11-Beta HSD1 in adipose tissue comprises:
   obtaining reductase activity of 11-Beta HSD1 in an isolated in vitro adipocyte cell population, and
   contacting said compound or composition with said adipocyte cell population.

3. The method of claim 1 wherein the compound or composition which inhibits said reductase activity of 11-Beta HSD1 in adipose tissue is carbenoxolone or a pharmaceutically acceptable salt thereof.

4. The method of claim 1, wherein said patient suffer from one of the following: obesity, insulin resistance, or obesity and insulin resistance.

5. A method for treating obesity, insulin resistance, or obesity and insulin resistance by regulating reductase activity of 11-Beta-hydroxysteroid dehydrogenase 1 (11-Beta HSD1) in adipose tissue in a patient in need thereof comprising
   determining reductase activity of 11 Beta HSD1 in adipose tissue,
   determining whether a compound or composition inhibits said reductase activity of 11 Beta HSD1 in adipose tissue, and
   administering to said patient said compound or composition which inhibits said reductase activity of 11-Beta HSD1 in adipose tissue, in an amount effective to so inhibit said reductase activity of 11-Beta HSD1 in adipose tissue.

* * * * *